(12) United States Patent
Gass et al.

(10) Patent No.: US 11,004,549 B2
(45) Date of Patent: May 11, 2021

(54) PATIENT OBJECT MAPPING TECHNIQUES

(71) Applicants: Varian Medical Systems, Inc, Palo Alto, CA (US); Varian Medical Systems International AG., Cham (CH)

(72) Inventors: Tobias Gass, Vogelsang (CH); Benjamin Haas, Brittnau (CH); Tomasz Morgas, Henderson, NV (US); Joao Neta, Birmenstorf (CH); Pawel Zak, Oberrohrdorf (CH); Yarema Mazuryk, Urdorf (CH)

(73) Assignees: Varian Medical Systems International AG, Cham (CH); Varian Medical Systems, Inc, Palo Alto, CA (US)

( * ) Notice: Subject to any disclaimer, the term of this patent is extended or adjusted under 35 U.S.C. 154(b) by 309 days.

(21) Appl. No.: 16/147,214

(22) Filed: Sep. 28, 2018

(65) Prior Publication Data
US 2020/0105385 A1    Apr. 2, 2020

(51) Int. Cl.
| | | |
|---|---|---|
| *G16H 10/60* | (2018.01) | |
| *G06F 16/28* | (2019.01) | |
| *G06F 3/0481* | (2013.01) | |
| *G06T 11/60* | (2006.01) | |

(52) U.S. Cl.
CPC .......... *G16H 10/60* (2018.01); *G06F 16/284* (2019.01); *G06F 3/04817* (2013.01); *G06T 11/60* (2013.01); *G06T 2200/24* (2013.01); *G06T 2210/41* (2013.01)

(58) Field of Classification Search
CPC ........ G16H 10/60; G16H 40/63; G16H 40/20; G16H 15/00; G16H 50/20; G16H 10/20; G16H 40/67; G16H 20/17; G16H 20/60; G16H 20/40; G16H 20/10; G16H 40/40; G06Q 10/10; G06Q 30/02; G06T 2200/24; G06N 20/00; G06F 8/65; G06F 19/00; G06F 3/04817; G06F 16/34; G06F 17/18
See application file for complete search history.

(56) References Cited

U.S. PATENT DOCUMENTS

| | | | |
|---|---|---|---|
| 2013/0041677 A1* | 2/2013 | Nusimow | .............. G16H 15/00 |
| | | | 705/2 |
| 2019/0037173 A1* | 1/2019 | Lee | ........................ H04W 76/10 |

FOREIGN PATENT DOCUMENTS

WO    2012052040    4/2012

* cited by examiner

Primary Examiner — Maroun P Kanaan

(57) ABSTRACT

Techniques for the mapping, selection and import of patient medical objects can include receiving metadata of a plurality of patient medical objects from one or more data sources. Metadata icons can be generated for the received metadata of the plurality of patient medical objects. The metadata icons can be filtered based on one or more received criteria. A patient map including the filtered metadata icons can be generated. In addition, the selection of one or more metadata icons in the patient map can be received and used to determine one or more selected patient medical objects. The selected patient medical objects can thereafter be imported from the one or more data sources.

14 Claims, 6 Drawing Sheets

PATIENT OBJECT MAPPING TECHNIQUES

BACKGROUND OF THE INVENTION

Computing systems have made significant contributions toward the advancement of modern society and are utilized in a number of applications to achieve advantageous results. Numerous devices, such as desktop personal computers (PCs), laptop PCs, tablet PCs, smart phones, servers, and the like have facilitated increased productivity and reduced costs in communicating and analyzing data in most areas of entertainment, education, business, and science. In the health care industry computing devices generate and store large amounts of data in the form of patient information, diagnosis, treatment plans, medical images (e.g., Computer Tomography (CT) scans, Magnetic Resonance Imaging (MRI), ultrasound images), geometric relations between images (e.g., registrations), delineations of organs, tumors and the like (e.g., structures), lab results, physician consultations, expert comments, and or the like, also referred to herein as patient medical objects. The patient medical objects can be stored on any number of different computing devices in various computing networks.

It can be difficult to find and download desired patient medical objects stored in various formats on various computing devices across one or more networks. Current solutions typically require a physician to select desired patient medical objects from table-based interfaces, such as network and file directories, from multiple sources explicitly. The systems may have limited filtering options for identifying the patient medical objects in such table-based interfaces. The desired patient medical objects are then typically downloaded to a local computing device used by the physician, before the physician can select and review them for use in a treatment plan for example. Accordingly, there is a continuing need for improved patient medical object selection and importing techniques.

SUMMARY OF THE INVENTION

The present technology may best be understood by referring to the following description and accompanying drawings that are used to illustrate embodiments of the present technology directed toward the mapping, selection and import of patient medical objects.

In one embodiment, a method of mapping patient medical objects can include receiving metadata of a plurality of patient medical objects from one or more sources. The metadata of the plurality of patient medical objects can be received without downloading the corresponding patient medical objects. Metadata icons can be generated for the metadata of the plurality of patient medical objects. The metadata icons and corresponding metadata of the plurality of patient medical objects can be stored in a relational data structure. One or more criteria can be received and used to filter the metadata icons. A patient map of the filtered metadata icons can be generated and displayed in a graphical user interface. The filtered metadata icons can be arranged in the patient map based on a creation date of the patient medical objects. The method can also include receiving a selection of one or more of the metadata icons in the displayed patient map. One or more selected patient medical objects corresponding to the selected one or more metadata icons can be determined from the relational data structure. The one or more selected patient medical objects can be imported from corresponding ones of the one or more data sources and displayed in a graphical user interface.

In another embodiment, a patient medical object mapping system can include a host unit, a display unit and a storage unit. The host unit can be configured to receive metadata of a plurality of patient medical objects from one or more data sources storing the plurality of patient medical objects. The host unit can generate metadata icons for the metadata of each of the plurality of patient medical objects. A mapping of the metadata icons and the corresponding metadata of the plurality of patient medical objects can be stored by the host unit in the storage unit. The host unit can generate a patient map including a subset of metadata icons determined from one or more received criteria. The subset of metadata icons can be arranged in the patient map based on a creation date of the corresponding patient medical objects. The patient map can also be stored by the host unit in the storage unit and or output in one or more graphical user interface. The host unit can also be configured to receive a selection of one or more of the metadata icons in the patient map. The host unit can determine one or more selected patient medical objects corresponding to the selected one or more metadata icons from the mapping of the metadata icons and the corresponding metadata of the plurality of patient medical objects stored in the storage unit. The host unit can be further configured to import one or more selected patient medical objects from corresponding sources. The imported patient medical objects can then be displayed in one or more graphical user interfaces.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

Embodiments of the present technology are illustrated by way of example and not by way of limitation, in the figures of the accompanying drawings and in which like reference numerals refer to similar elements and in which.

DETAILED DESCRIPTION OF THE INVENTION

Figure 1A:
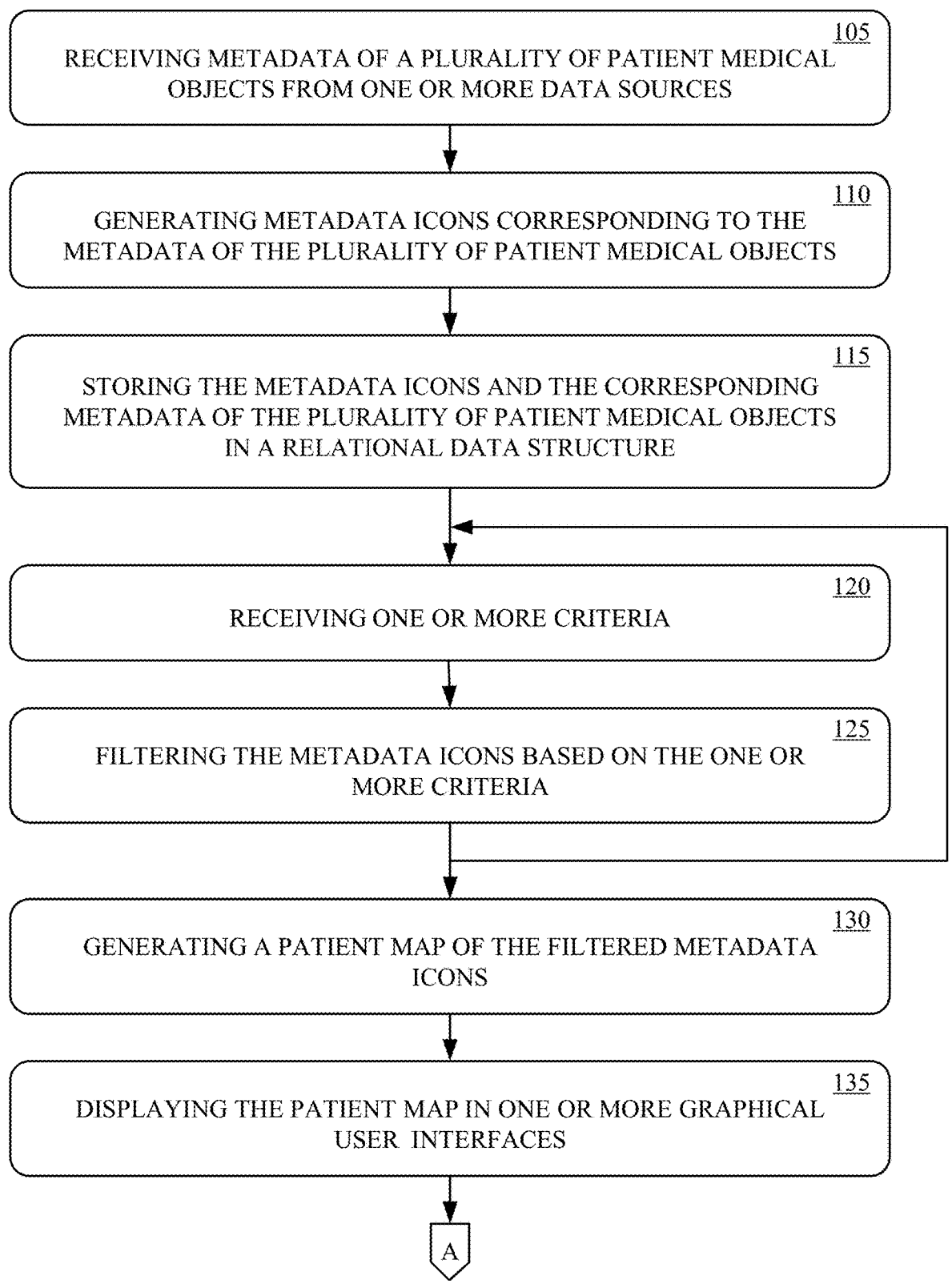
FIGS. 1A and 1B show a patient medical object mapping, selection and import method, in accordance with aspects of the present technology.

Reference will now be made in detail to the embodiments of the present technology, examples of which are illustrated in the accompanying drawings. While the present technology will be described in conjunction with these embodiments, it will be understood that they are not intended to limit the invention to these embodiments. On the contrary, the invention is intended to cover alternatives, modifications and equivalents, which may be included within the scope of the invention as defined by the appended claims. Furthermore, in the following detailed description of the present technology, numerous specific details are set forth in order to provide a thorough understanding of the present technology. However, it is understood that the present technology may be practiced without these specific details. In other instances, well-known methods, procedures, components, and circuits have not been described in detail as not to unnecessarily obscure aspects of the present technology.

Some embodiments of the present technology which follow are presented in terms of routines, modules, logic blocks, and other symbolic representations of operations on data within one or more electronic devices. The descriptions and representations are the means used by those skilled in the art to most effectively convey the substance of their work to others skilled in the art. A routine, module, logic block and/or the like, is herein, and generally, conceived to be a self-consistent sequence of processes or instructions leading to a desired result. The processes are those including physical manipulations of physical quantities. Usually, though not necessarily, these physical manipulations take the form of electric or magnetic signals capable of being stored, transferred, compared and otherwise manipulated in an electronic device. For reasons of convenience, and with reference to common usage, these signals are referred to as data, bits, values, elements, symbols, characters, terms, numbers, strings, and/or the like with reference to embodiments of the present technology.

It should be borne in mind, however, that all of these terms are to be interpreted as referencing physical manipulations and quantities and are merely convenient labels and are to be interpreted further in view of terms commonly used in the art. Unless specifically stated otherwise as apparent from the following discussion, it is understood that through discussions of the present technology, discussions utilizing the terms such as "receiving," and/or the like, refer to the actions and processes of an electronic device such as an electronic computing device that manipulates and transforms data. The data is represented as physical (e.g., electronic) quantities within the electronic device's logic circuits, registers, memories and/or the like, and is transformed into other data similarly represented as physical quantities within the electronic device.

In this application, the use of the disjunctive is intended to include the conjunctive. The use of definite or indefinite articles is not intended to indicate cardinality. In particular, a reference to "the" object or "a" object is intended to denote also one of a possible plurality of such objects. It is also to be understood that the phraseology and terminology used herein is for the purpose of description and should not be regarded as limiting.

Figure 1B:
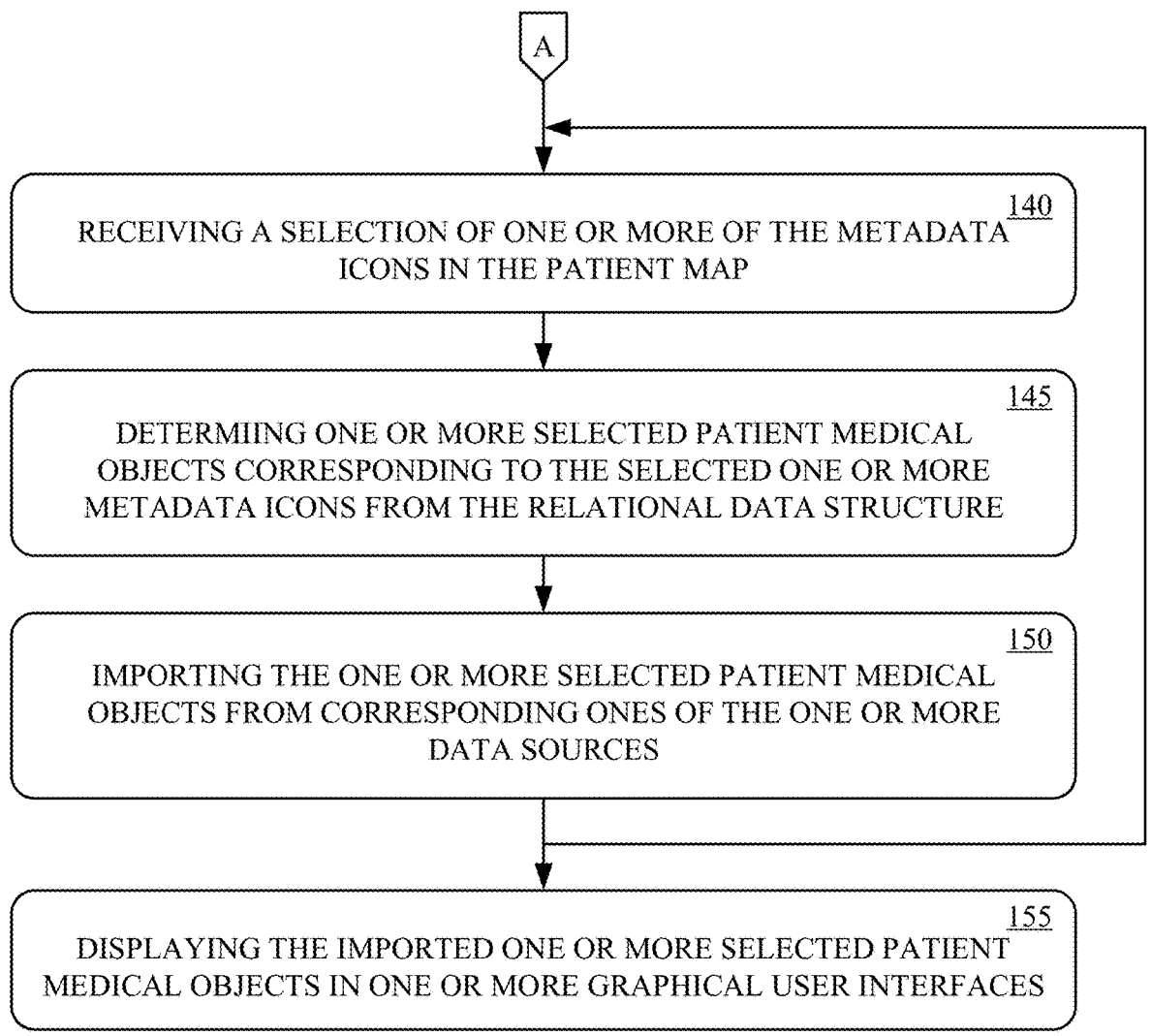

FIGS. 1A and 1B show a patient medical object mapping, selection and import method, in accordance with aspects of the present technology. The method may be implemented as computing device-executable instructions (e.g., computer program) that are stored in computing device-readable storage medium (e.g., computer memory) and executed by a computing device (e.g., processor). The patient medical object mapping, selection and import method will be further described with reference to FIG. 2, which shows an exemplary patient medical object computing platform.

In aspects, the patient medical object mapping can include receiving metadata for a plurality of patient medical objects from one or more data sources, at 105. The patient medical objects can include various patient medical images, such as Computer Tomography (CT) scan images, Magnetic Resonance Imaging (MRI) scan images, Positron-Emission Tomography (PET) images, ultrasound images, and the like. In other examples, the patient medical objects can include geometric relations between images (commonly referred to as registrations), delineations of organs, tumors and the like (commonly referred to as structures), diagnosis, consultations, treatment plans, expert comments, lab results, and the like. The above examples of patient medical objects are not intended to be exhaustive or to limit aspects of the present technology. The patient medical objects can be received from any number of sources, including but not limited to data servers, cloud storage, disk drives, computers, application databases, network folders, information systems, medical instruments, and or the like. The metadata is data that provides information about the patient medical objects, such as date of capture, creation or acquisition of the corresponding patient medical object, the source location of the corresponding patient medical object, and the like. The metadata can also include thumbnails, previews, summaries or the like of corresponding patient medical objects. The metadata can also include indicators of a type, format or the like of the patient medical object. The metadata can also include relations between a corresponding patient medical object and one or more other patient medical objects. The above examples of metadata are not intended to be exhaustive or to limit aspects of the present technology.

Figure 2:
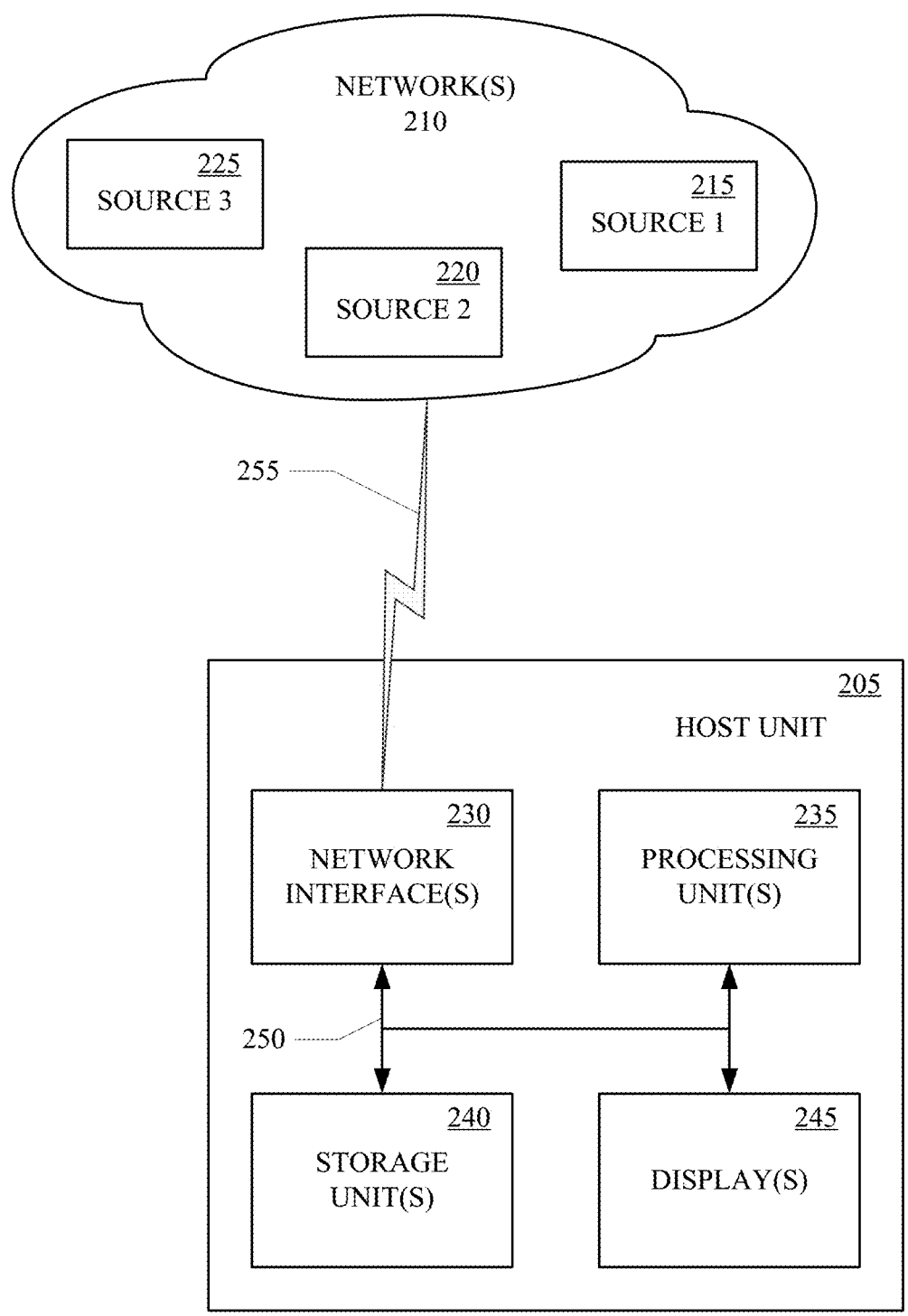
FIG. 2 shows a patient medical object computing platform, in accordance with aspects of the present technology.

In one example, a host unit 205 can be communicatively coupled to one or more networks 210 including one or more sources 215-225 of patient medical objects, as illustrated in FIG. 2. The host unit 205 can include one or more network interfaces 230, one or more processing units 235, one or more storage units 240 and one or more displays 245 communicatively coupled together by one or more buses 250. Although illustrated as integral to the host unit 205, the one or more storage units 240 can include peripheral storage units such as external hard drives. The one or more storage units 240 can also include network storage or cloud storage associated with the host unit 205. The one or more network interfaces 230 and one or more network communication links 255 can communicatively couple the host unit 205 to the one or more sources 215-225. One or more sets of instructions stored in the storage unit 240 can configure the host unit to query, crawl, search or the like, one or more sources 215-225 of patient medical objects for a given patient in one or more networks 210. In response, the host unit 205 can receive metadata for a plurality of patient medical objects of the given patient. The host unit 205 can be configured to receive the metadata of the plurality of patient medical objects from the one or more sources without downloading the patient medical objects.

At 110, metadata icons corresponding to the metadata of the plurality of patient medical objects can be generated. For example, the host unit 205 can be configured to generate metadata icons including a thumbnail of a patient medical image, a summary of a treatment plan, or the like. The metadata icon can also include one or more indicators of a type, format or the like of the corresponding patient medical object. For example, the shape, background color, border or the like can indicate the type or format of the corresponding patient medical object.

At 115, the metadata icons and the corresponding metadata of the plurality of patient medical objects can be stored. For example, the host unit 205 can be configured to store a mapping of the metadata icons and the corresponding metadata of the plurality of patient medical objects in a storage unit 240 associated with the host unit 205. In another example, the host unit 205 can store the metadata icons and the corresponding metadata in a relational data structure on the storage unit 240.

At 120, one or more criteria can be received. For example, the host unit 205 can receive a criteria such as an indicator of a Radiation Therapy (RT) context. In another case, the host can receive an indicator of a chemotherapy context. At 125, the metadata icons can be filtered based on the one or more received criteria. For example, the host unit 205 can filter the metadata icons that relate to Radiation Therapy (RT) context to identify patient medical objects such as Computer Tomography (CT) scan images, registrations, structures, treatment plans, consulting physician reviews, expert comments and the like. Various criteria can be received one or more times during the patient medical object mapping, selection and import process. In such case the process of filtering the metadata 125 can be repeated in response to receipt of one or more new, updated or different criteria 120.

At 130, a patient map can be generated based on the filtered metadata icons. For example, the host unit 205 can be configured to generate a patient map by arranging the filtered metadata icons in a predetermined arrangement. The filtered metadata icons can be arranged, for example, along a timeline of the patient map in an order of the acquisition date of the corresponding patient medical objects. An acquisition date of the corresponding patient medical objects, contained in the metadata, can be displayed along the timeline of the patient map. The filtered metadata icons can also be further arranged in the patient map to illustrate relationships between the corresponding patient medical objects. For instance, a series of CT scans including different levels of details can be arranged in the patient map in a hierarchical structure according to the different levels of details. In another instance, delineations and/or registrations can be arranged adjacent corresponding images. In another instance, the filtered metadata icons can be spaced along the timeline to indicate the relative time periods between the acquisition dates of the corresponding patient medical objects.

At 135, the patient map can be displayed in one or more graphical user interfaces. For example, the host unit 205 can output the generated patient map in a first graphical user interface on one or more displays 245. The displayed patient map can make it easy for a physician to select images for Radiation Therapy (TR) planning. For example, various levels of detail can be revealed by zooming in and out on the patient map in the graphical user interface. For instance, when zoomed out, a series of four-dimensional (4D) CT scans can be represented by a thumbnail image indicating that the patient medical object is a 4D CT scan. By zooming in, the metadata icon can represent the forty images as sets of four different respiratory CT scans for ten successive respiratory cycles. Zooming in and out on the patient map can also adjust the time range along the time axis of the patient map that is displayed in the graphical user interface.

The metadata icons in the patient map can present the information about the corresponding patient medical objects in a consistent form. A physician can also readily recognize images and their purpose from the metadata icons in the patient map. The patient map of the metadata icons can also be generated from the metadata of the patient medical objects without the need to download the patient medical object.

Figure 3:
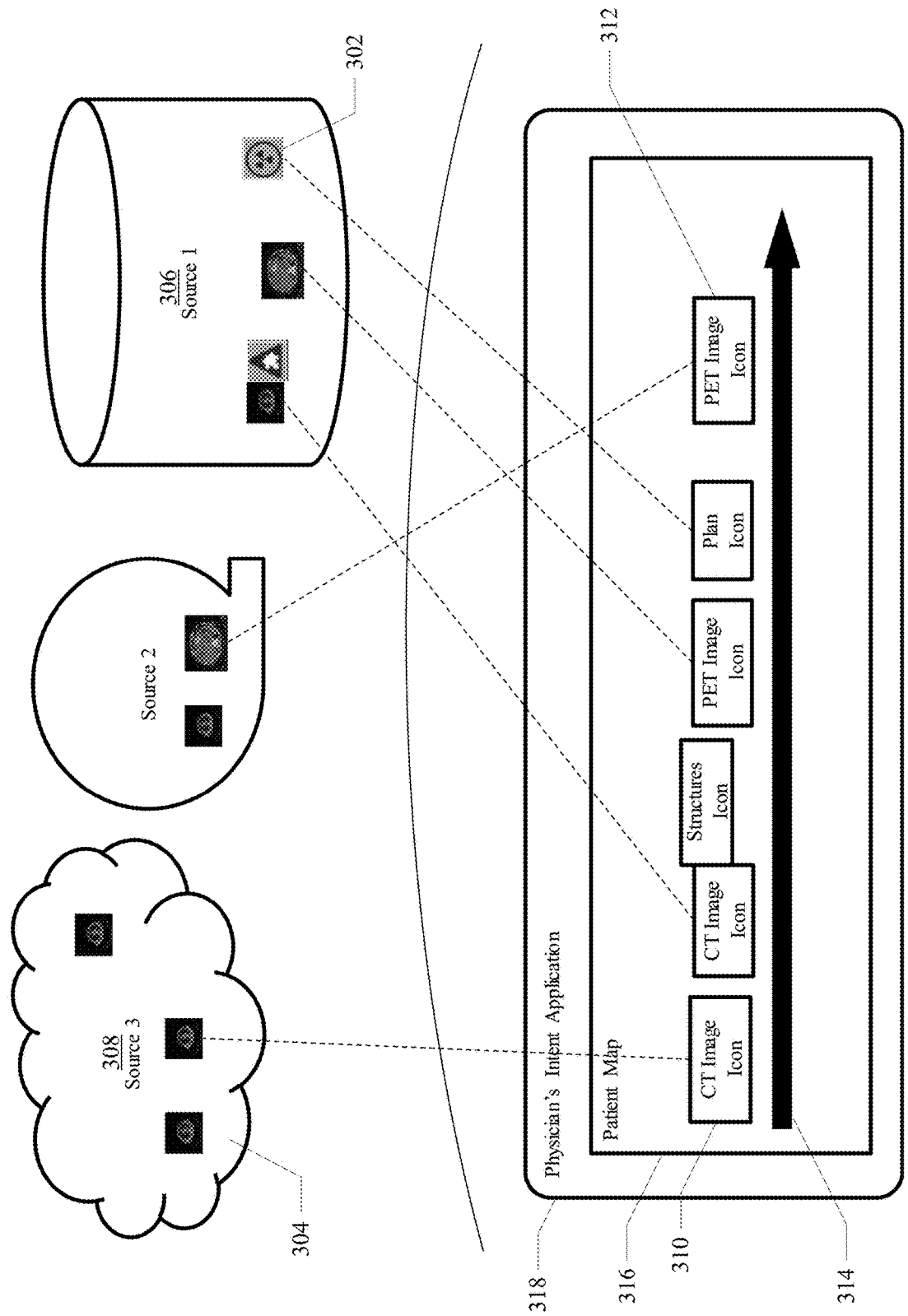
FIG. 3 illustrates a patient medical object mapping process, in accordance with aspects of the present technology.

Referring now to FIG. 3, an exemplary patient medical object mapping process, in accordance with aspects of the present technology, is illustrated. In the illustrated example, a plurality of patient medical objects 302-304 can be associated with a number of different sources. Metadata icons 310-312 corresponding to a subset of the plurality of patient medical objects 302-304 filtered according to one or more criteria can be arranged along a timeline 314 in a patient map 316 displayed in a graphical user interface of an exemplary application 318. The patient map can make it easier for a user to identify and select patient medical objects. For example, the physician can see what relevant patient medical objects are available, such as CT images, PET images, structures, treatment plans and the like. In another example, the physician can zoom in and out on the mapping, causing the organization of the metadata icons to change in a context specific way such that grouping, relationships and the like expand or collapse depending upon the level of detail for the particular zoom level. The physician can also see the relation between a given structure and a given CT image. The physician can also see if the patient medical objects are current or if they are outdated and new patient medical objects need to be obtained. The physician can obtain and review the overview of the patient medical objects represented by the metadata icons in the patient map without the need to separately search different sources of the data and without the need to download the patient medical objects from the various sources.

Figure 4:
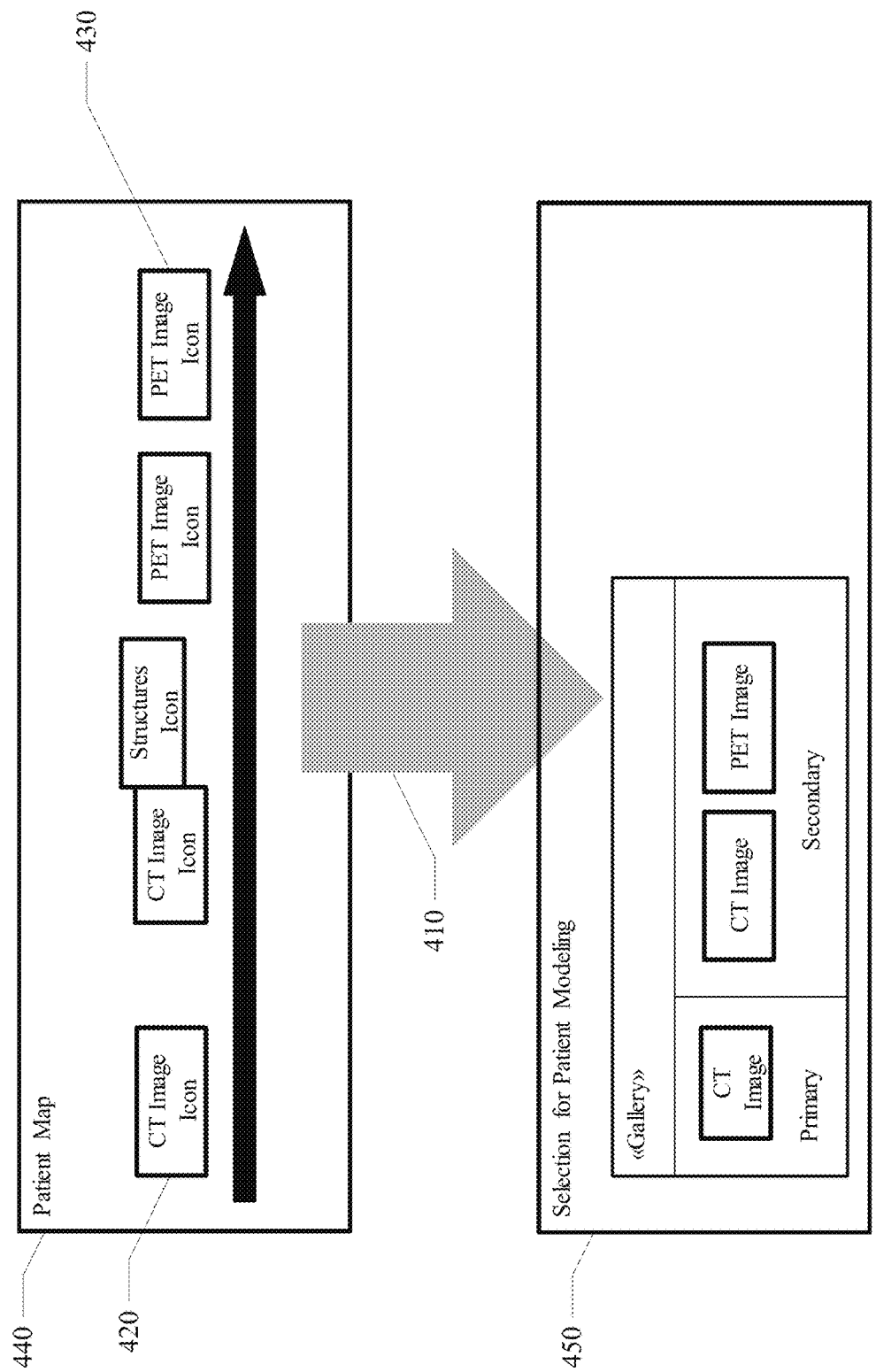
FIG. 4 illustrates a patient medical object selection process, in accordance with aspects of the present technology.

Referring now to FIG. 1B, the patient medical object selection and import process can include receiving an indication of a selection of one or more of the metadata icons in the patient map, at 140. For example, the host unit 205 can be configured to receive one or more inputs associated with a physician dragging 410 one or more of the metadata icons 420-430 on the patient map 440 to a graphical user interface of a patient modeling application 450, as illustrated in FIG. 4.

At 145, one or more selected patient medical objects corresponding to the selected one or more metadata icons can be determined from the stored mapping, relational data structure or the like. For example, the host unit 205 can index the selected one or more metadata icons in the relational data structure in the local storage unit 240 to determine the corresponding selected patient object and its location in a given one of the one or more sources.

At 150, the one or more selected patient medical objects can be imported from corresponding ones of the one or more data sources. In one example, the host unit 205 can be configured to download the one or more selected patient medical objects from the corresponding ones of the one or more data sources. The host unit 205 can convert the downloaded patient medical objects from a source format to a destination format associated. The medical object in the destination format can then be stored by the host unit 205 in the storage unit 240 associated with the host unit 205 or an application. The selection of metadata icons in the patient map can be received one or more times during the patient medical object mapping, selection and import method. In such case the process of determining corresponding selected patient medical objects 145 and importing the determined selected patient medical objects 150 can be repeated each time in response to receipt of one or more new, updated or different selections of metadata icons from the patient map is received 140.

At 155, the imported one or more selected patient medical objects can be displayed in one or more graphical user interfaces. For example, the host unit 205 can be configured to output the imported patient medical objects in a second graphical user interface on one or more displays 245. In addition, two or more imported medical objects can be combined by the host unit 205 to generate a composite patient medical object. The host unit 205 can also output the composite patient medical object in the second graphical user interface.

For example, as illustrated in FIG. 4, a physician can drag a given CT image icon from the patient map 440 and drop it into a selection area associated with patient modeling 450 to select the corresponding patient medical object for import as a primary image into a patient modeling application. In addition, the physician can also drag one or more other metadata icons from the patient map 440 into the selection area to import the corresponding patient medical objects as secondary images.

Figure 5:
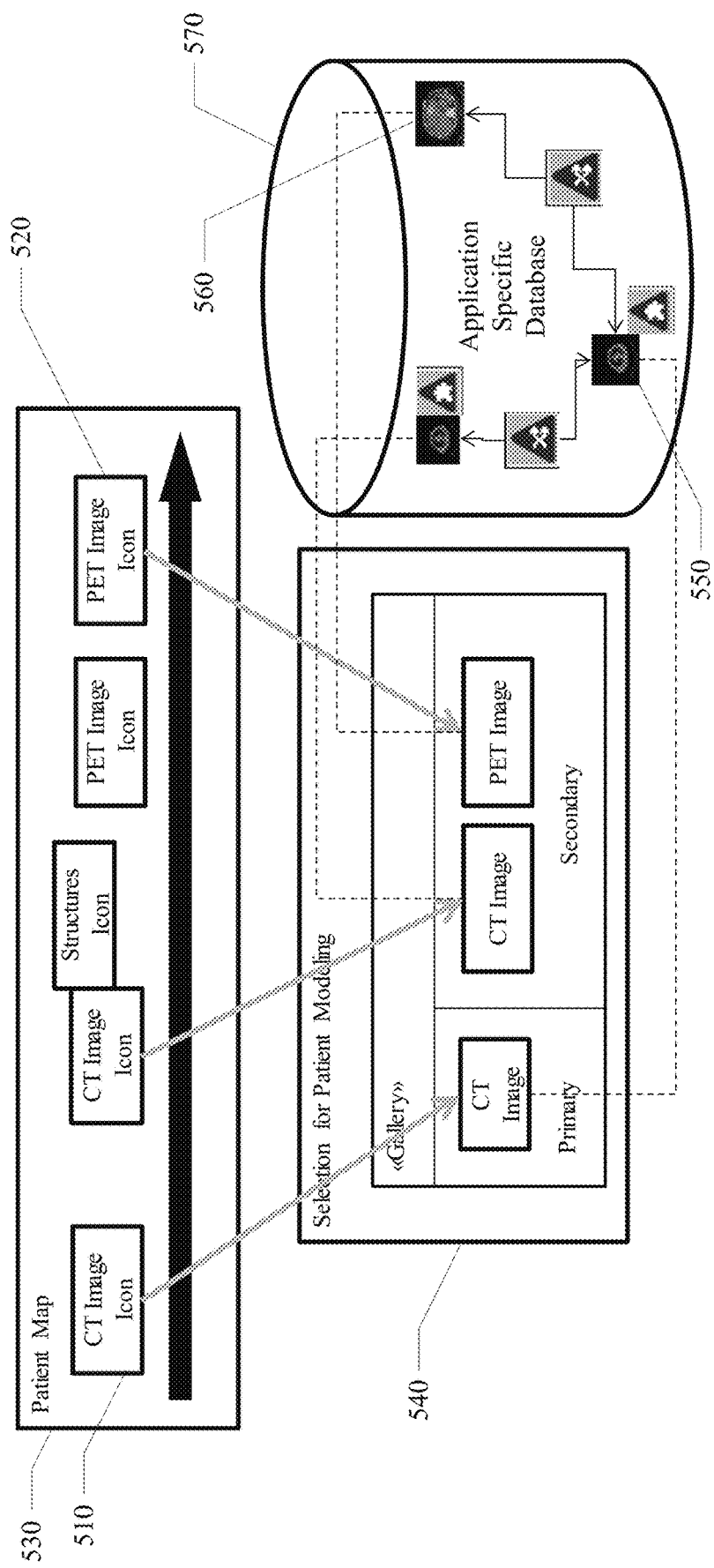
FIG. 5 illustrates a patient medical object import process, in accordance with aspects of the present technology.

Referring now to FIG. 5, an exemplary patient medical object import process, in accordance with aspects of the present technology, is illustrated. In the illustrated example, a physician can drag a given CT image icon 510 from the patient map 530 and drop it into the patient modeling selection area 540. In response to the CT image icon 510 being selected, the corresponding patient medical images 550 can be imported into a data structure 570 stored in a storage unit associated with the host unit or another application. While the given CT image 510 is being imported into the data structure and assigned as the primary image in the patient modeling application area 540, the physician can drag and drop other metadata icons from the patient map into the patient modeling selection area 540. The secondary images can then be imported and stored in the data structure 570 as they are dropped into the patient modeling selection area 540. In addition, the primary image can be displayed while the secondary images are being imported. Accordingly, a user can interface with the metadata icons in the patient map independently of the import status of the corresponding patient medical object.

Aspects of the present technology advantageously allow a user, such as a physician, to obtain an overview and visualization of data for a specific patient. The patient map advantageously aggregates and displays a large amount of filtered data in a convenient form which can reduce the mental workload on users. The collection and display of metadata icons in the patient map can also be performed without downloading the corresponding patient medical images, which can advantageously reduce network traffic, processing workload, and user waiting time. The patient map can also enable the selection and import of patient medical objects in single user interaction.

The foregoing descriptions of specific embodiments of the present technology have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the present technology and its practical application, to thereby enable others skilled in the art to best utilize the present technology and various embodiments with various modifications as are suited to the particular use contemplated. It is intended that the scope of the invention be defined by the claims appended hereto and their equivalents.

What is claimed is:

1. A method of mapping patient medical objects comprising:
    receiving metadata of a plurality of patient medical objects across a network by a host from one or more data sources without downloading the plurality of patient medical objects from the one or more data sources;
    generating metadata icons by the host for the metadata of the plurality of patient medical objects;
    storing the metadata icons and the corresponding metadata by the host in a relational data structure;
    receiving by the host one or more criteria;
    filtering the metadata icons by the host based on the one or more received criteria;
    generating by the host a patient map of the filtered metadata icons;
    displaying by the host the patient map in a first graphical user interface;
    receiving by the host a selection of one or more of the metadata icons in the patient map;
    determining by the host one or more selected patient medical objects corresponding to the selected one or more metadata icons from the relational data base;
    importing by the host the one or more selected patient medical objects from corresponding ones of the one or more data sources across the network, wherein a primary one of the selected patient medical objects is imported before secondary ones of the selected patient medical objects; and
    displaying by the host the imported one or more selected patient medical objects in a second graphical user interface, wherein the imported primary one of the selected patient medical objects is displayed while the secondary ones of the selected the selected patient medical objects are imported.

2. The method according to claim 1, wherein the filtered metadata icons are arranged in the patient map based on a creation date of the patient medical objects.

3. The method according to claim 1, wherein importing the one or more selected patient medical objects comprises:
    downloading the one or more selected patient medical objects from corresponding ones of the one or more source data sources;
    converting the downloaded one or more selected patient medical objects from a source format to a destination format; and
    storing the downloaded one or more selected medical objects in the destination format in a destination storage unit.

4. The method according to claim 1, wherein the patient map includes one or more indicators of relationships between the corresponding patient medical objects.

5. The method according to claim 1, wherein the patient map includes one or more indicators of one or more types of the corresponding patient medical objects.

6. The method according to claim 1, further comprising:
    receiving a time range indicator; and
    displaying the patient map in the first graphical user interface adjusted based on the received time range indicator.

7. The method according to claim 6, wherein the time range indicator includes a zoom level.

8. The method according to claim 1, further comprising:
    receiving a context indicator; and
    displaying the patient map in the first graphical user interface adjusted based on the received context indicator.

9. The method according to claim 1, further comprising:
    receiving a level of detail indicator; and
    displaying the patient map in the first graphical user interface wherein a grouping of two or more of the filtered metadata icons is adjusted based the level of detail indicator.

10. A patient medical object mapping system comprising:
    a display unit;
    a storage unit; and
    a host unit configured to;
        receive metadata of a plurality of patient medical objects from one or more data sources storing the plurality of patient medical objects without downloading the plurality of patient medical objects to the host;
generate metadata icons for the metadata of the plurality of patient medical objects;
storing a mapping of the metadata icons and the corresponding metadata in the storage unit;
generate a patient map including a subset of the metadata icons and arranged based on a creation date of the corresponding patient medical objects;
store the patient map in the storage unit;
display the patient map on the display unit;
receive a selection of one or more of the metadata icons in the patient map;
determine one or more selected patient medical objects corresponding to the selected one or more metadata icons from the mapping of the metadata icons and the corresponding metadata of the plurality of patient medical objects stored in the storage unit;
import the one or more selected patient medical objects from corresponding ones of the one or more data sources, wherein a primary one of the selected patient medical objects is imported before secondary ones of the selected patient medical objects; and
display the imported one or more selected patient medical objects on the display unit, wherein the imported primary one of the selected patient medical objects is displayed while the secondary ones of the selected the selected patient medical objects are imported.

11. The device of claim 10, wherein the host unit is further configured to;
combine two or more imported selected medical objects to generate a composite patient medical object; and
display the composite patient medical object on the display unit.

12. One or more non-transitory computing device-readable storage mediums storing instructions executable by one or more computing devices to perform a method of mapping patient medical objects comprising:
receiving metadata of a plurality of patient medical objects from one or more data sources without downloading the plurality of patient medical objects;
generating metadata icons for the received metadata of the plurality of patient medical objects;
generating a relational data structure including the metadata icons and the corresponding metadata of the plurality of patient medical objects;
receiving one or more criteria;
filtering the metadata icons based on the one or more received criteria;
generating a patient map of the filtered metadata icons;
outputting the patient map in a graphical user interface;
receiving a selection of one or more of the metadata icons in the patient map;
determining one or more selected patient medical objects corresponding to the selected one or more metadata icons from the relational data base;
importing the one or more selected patient medical objects from corresponding ones of the one or more data sources, wherein a primary one of the selected patient medical objects is imported before secondary ones of the selected patient medical objects; and
displaying the imported one or more selected patient medical objects in a second graphical user interface, wherein the imported primary one of the selected patient medical objects is displayed while the secondary ones of the selected the selected patient medical objects are imported.

13. The one or more non-transitory computing device-readable storage mediums storing instructions executable by the one or more computing devices to perform the method of mapping patient objects according to claim 12, wherein the filtered metadata icons are arranged in the patient map based on a creation date of the patient medical objects, wherein the creation date is included in the metadata of the plurality of patent medical objects.

14. The one or more non-transitory computing device-readable storage mediums storing instructions executable by the one or more computing devices to perform the method of mapping patient objects according to claim 12, wherein importing the one or more selected patient medical objects comprises:
downloading the one or more selected patient medical objects from corresponding ones of the one or more data sources;
converting the downloaded one or more selected medical objects from a source format to a destination format; and
storing the downloaded one or more selected medical objects in the destination format.

* * * * *